(12) United States Patent
Sugden et al.

(10) Patent No.: US 6,811,983 B2
(45) Date of Patent: Nov. 2, 2004

(54) METHOD OF IDENTIFYING INHIBITORS OF EBNA-1

(75) Inventors: William M. Sugden, Madison, WI (US); Atsushi Jun Komano, Tokyo (JP); Gregory Kennedy, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/201,887

(22) Filed: Jul. 24, 2002

(65) Prior Publication Data

US 2003/0099936 A1 May 29, 2003

Related U.S. Application Data

(60) Provisional application No. 60/308,159, filed on Jul. 26, 2001.

(51) Int. Cl.$^7$ ................................................. C12Q 1/68
(52) U.S. Cl. .......................... 435/6; 435/7.1; 435/91.33; 435/69.1
(58) Field of Search ............................. 435/91.33, 69.1, 435/6, 7.1

(56) References Cited

PUBLICATIONS

Cohen, J. I., Wang, F., Mannick, J., and Kieff, E. (1989). Epstein–Barr virus nuclear protein 2 is a key determinant of lymphocyte transformation, Proc. Natl. Acad. Sci. USA 86, 9558–62.

Gahn, T. A., and Sugden, B. (1995). An EBNA–1–dependent enhancer acts from a distance of 10 kilobase pairs to increase expression of the Epstein–Barr virus LMP gene, J. Virol. 69, 2633–6.

Hammerschmidt, W., and Sugden, B. (1989). Genetic analysis of immortalizing functions of Epstein–Barr virus in human B lymphocytes, Nature 340, 393–7.

Kang, M. S., Hung, S. C., and Kieff, E. (2001). Epstein–Barr virus nuclear antigen 1 activates transcription from episomal but not integrated DNA and does not alter lymphocyte growth, Proc. Natl. Acad. Sci. USA 98, 15233–8.

Kaye, K. M., Izumi, K. M., and Kieff, E. (1993). Epstein–Barr virus latent membrane protein 1 is essential for B–lymphocyte growth transfromation, Proc. Natl. Acad. Sci. USA 90, 9150–4.

Kempkes, B., Spitkovsky, D., Jansen–Durr, P., Ellwart, J. W., Kremmer, E., Delecluse, H. J., Rottenberger, C., Bornkamm, G. W., and Hammerschmidt, W. (1995). B–cell proliferation and induction of early G1–regulating proteins by Epstein–Barr virus mutants conditional for EBNA2, EMBO J. 14, 88–96.

Kilger, E., Kieser, A., Baumann, M., and Hammerschmidt, W. (1998). Epstein–Barr virus–mediated B–cell proliferation is dependent upon latent membrane protein 1, which simulates an activated CD40 receptor, EMBO J. 17, 1700–9.

Kirchmaier, A. L., and Sugden, B. (1997). Dominant–negative inhibitors of EBNA–1 of Epstein–Barr virus, J. Virol. 71, 1766–75.

Mackey, D., and Sugden, B. (1997). Studies on the mechanism of DNA linking by Epstein–Barr virus nuclear antigen 1, J. Biol. Chem. 272, 29873–29879.

Mackey, D., and Sugden, B. (1999). The linking regions of EBNA1 are essential for its support of replication and transcription, Mol. Cell Biol. 19, 3349–59.

Sugden, B., and Warren, N. (1989). A promoter of Epstein–Barr virus that can function during latent infection can be transactivated by EBNA–1, a viral protein required for viral DNA replication during latent infection, J. Virol. 63, 2644–9.

Tomkinson, B., Robertson, E., and Kieff, E. (1993). Epstein–Barr virus nuclear proteins EBNA–3A and EBNA–3C are essential for B–lymphocyte growth transformation, J. Virol. 67, 2014–25.

Zimber–Strobl. U., Kempkes, B., Marschall, G., Zeidler, R., Van Kooten, C. Banchereau, J., Bornkamm, G. W., and Hammerschmidt, W. (1996). Epstein–Barr virus latent membrane protein (LMP1) is not sufficient to maintain proliferation of B cells but both it and activated CD40 can prolong their survival, EMBO J. 15, 7070–8.

*Primary Examiner*—Ali R. Salimi
(74) *Attorney, Agent, or Firm*—Quarles & Brady LLP

(57) ABSTRACT

A method of assaying potential inhibitors of EBNA-1 is disclosed. In one aspect, this invention comprises the steps of (a) obtaining an EBV-positive cell line and an EBV-negative cell line; (b) exposing the cell lines to a test compound, and (c) observing the effect of the compound on induction of apoptosis in the cell lines, wherein significant apoptosis in the EBV-positive cell line and lack of significant apoptosis in the EBV-negative cell line indicates a compound that specifically inhibits EBNA-1.

9 Claims, 5 Drawing Sheets

Fig. 3
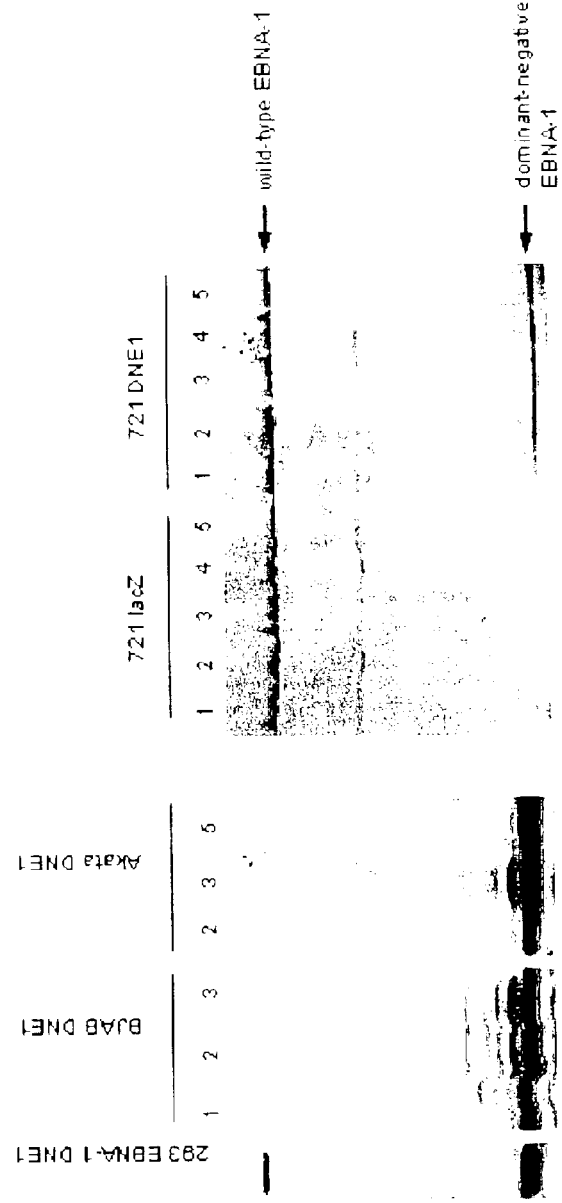
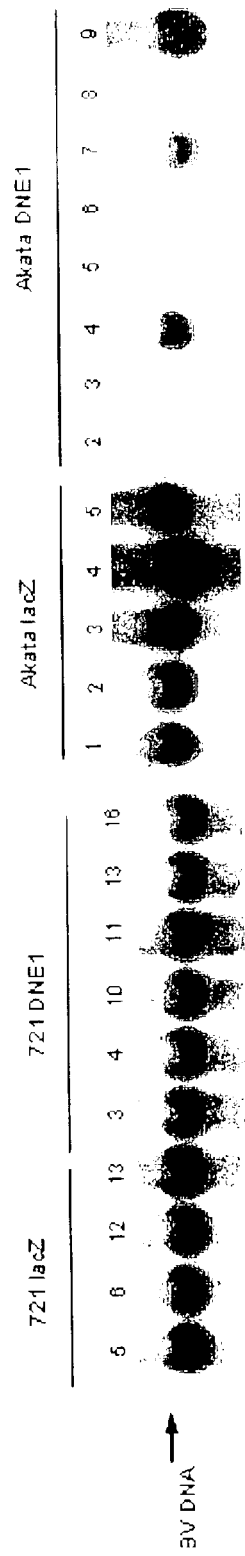

METHOD OF IDENTIFYING INHIBITORS OF EBNA-1

CROSS-REFERENCE TO RELATED APPLICATION

This application claims priority to U.S. Ser. No. 60/308,159, filed Jul. 26, 2001, which is incorporated by reference herein.

STATEMENT REGARDING FEDERALLY SPONSORED RESEARCH OR DEVELOPMENT

This invention was made with United States government support awarded by the following agencies: NIH CA22443. The United States has certain rights in this invention.

BACKGROUND OF THE INVENTION

Epstein-Barr virus (EBV) contributes causally to Burkitt's lymphoma, nasopharyngeal carcinoma, and B-cell lymphomas in immunocompromised individuals (de-The, et al., 1978; Hanto, et al., 1981; Zeng, et al., 1983; Zeng, 1985). EBV may also contribute causally to a portion of T-cell lymphomas, Hodgkin's disease, gastric carcinomas, and, possibly even, breast carcinoma (Bonnet, et al., 1999; Fina, et al., 2001; Glaser, et al., 1997;Imai, et al., 1994; Siebert, et al., 1995; Shibata and Weiss, 1992; Tokunaga, et al., 1993). The growing number of malignancies potentially associated with EBV drives our need to understand EBV's biology in order to develop specific therapeutic tools to treat its associated cancers.

EBV establishes a latent infection in human cells, in which its DNA is maintained extrachromosomally with only a limited number of its genes being expressed (reviewed in Rowe, 1999). Among them, EBV nuclear antigen-1 (EBNA-1) is the only viral gene known to be expressed as a protein in all EBV-associated tumor cells. EBNA-1 dimerizes and binds specifically to two clusters of its cognate sites within the origin of DNA synthesis of EBV's replicon, oriP. EBNA-1's binding to oriP has been shown to promote both the initiation of DNA synthesis and the extrachromosomal maintenance of small replicons derived from EBV in proliferating cells (Rawlins, et al., 1985; Yates, et al., 1985). EBNA-1 contributes to the initiation of DNA synthesis at oriP by associating directly or indirectly with ORC and the MCM complex (Chaudhuri, et al., 2001; Schepers, et al., 2001)). EBNA-1 also enhances transcription from promoters near oriP that drive expression of the viral genes EBNA-2, EBNA-3a, EBNA-3c, and latent membrane protein-1 (LMP-1), all of which are known to be required for the initiation and/or maintenance of proliferation of EBV-immortalized B cells (Cohen, et al., 1989; Gahn and Sugden, 1995; Hammerschmidt and Sugden, 1989; Kaye, et al., 1993; Kempkes, et al., 1995; Kilger, et al., 1998; Sugden and Warren, 1989; Tomkinson, et al., 1993; Zimber-Strobl, et al., 1996). These observations make it likely that EBNA-1's functions are required for EBV-infected cells to proliferate. However, what EBNA-1 contributes to those tumor cells in which it is expressed alone is unknown.

BRIEF SUMMARY OF THE INVENTION

In one embodiment, the present invention is a method assaying potential inhibitors of EBNA-1 comprising the steps of (a) obtaining an EBV-positive cell line and an EBV-negative cell line; (b) exposing the cell lines to a test compound, and (c) observing the effect of the compound on induction of apoptosis in the cell lines, wherein significant apoptosis in the EBV-positive cell line and lack of significant apoptosis in the EBV-negative cell line indicates a compound that specifically inhibits EBNA-1.

In a particularly advantageous form of the present invention, the EBV-positive cell line comprises 721 cells and the EBV-negative cell comprise BJAB cells.

It is an object of the present invention to assay potential inhibitors of EBNA-1.

Other objects, features and advantages of the present invention will become apparent to one of skill in the art after examination of the specification, claims and drawings.

BRIEF DESCRIPTION OF THE SEVERAL VIEWS OF THE DRAWINGS

(FIG. 1A) The structures of the wild-type EBNA-1 and of a dominant-negative derivative of EBNA-1, DNE1, used in this study are shown. (FIG. 1B) The structures of retroviral vectors used in this study are shown. The 5' long terminal repeat (5'LTR) drives transcription of either lacZ or DNE1 and the green fluorescent protein (GFP). The packaging signal is shown as $\Psi$. (FIG. 1C) The experimental approach is diagrammed along with the flow cytometric profiles of 721 cells infected with the DNE1-virus before and after sorting for GFP.

FIG. 3. Viral antigens and DNA in infected, sorted cells. (FIG. 3A) Detection of the wild-type EBNA-1 and the dominant-negative EBNA-1 (DNE1) in 293/EBNA-1 cells transiently transfected with the DNE1-retroviral vector and in BJAB, Akata, and 721 clones infected with either the lacZ- or DNE1-virus detected by Western blot analysis. Shown are the clone numbers. (FIG. 3B) Detection of Bam HI W fragment of EBV in 721 and Akata clones infected with either the lacZ- or DNE1-virus by Southern blot analysis. Shown are the clone numbers.

(FIG. 4A) EBV-positive 721 cells infected with the DNE1-virus grew slowly relative to infected EBV-negative BJAB cells and LacZ-infected 721 cells. The percentage of apoptotic cells in DNE1-virus-infected 721 cells was higher at all time points than for the other cells as demonstrated by a morphological examination (FIG. 4F) or an immunofluorescent assay detecting active caspase-3 (FIG. 4G). (FIGS. 4B–E) 721 and AG876-J1 cells at 6 to 7 days following infection with either the lacZ- or DNE1-virus were stained with acridine orange. The nuclear morphology characteristic of apoptotic cells (arrowheads) was more frequently observed in 721 (FIGS. 4B and C) and AG876-J1 (FIGS. 4D and E) cells infected with the DNE1-virus (FIGS. 4C and E) than in those infected with the lacZ-virus (FIGS. 4B and D).

DETAILED DESCRIPTION OF THE INVENTION

Figure 1:
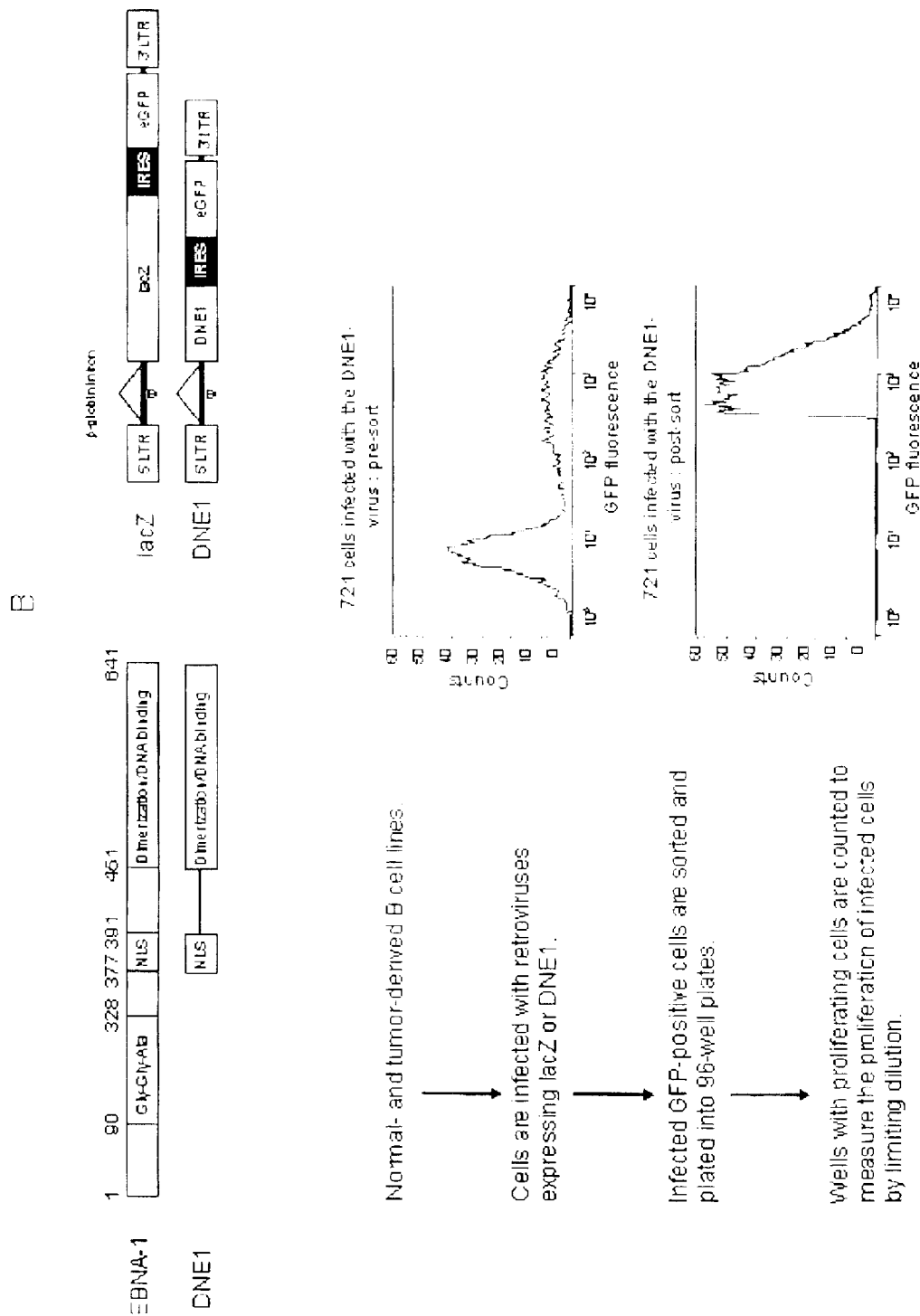
FIG. 1. An outline of the experimental approach.

The present invention is a method of screening potential inhibitors of EBNA-1 and is based on our new findings that inhibition of EBNA-1 induces apoptosis and that one may use the induction of apoptosis as an assay for inhibitors of EBNA-1. Preferably, the method comprises the steps of obtaining an EBV-positive cell line and EBV-negative cell line and exposing the cell lines to a test compound. One would then observe the effect of the compound on the induction of apoptosis in the EBV-positive cell line. Apoptosis of the EBV-positive cell line and no apoptosis of the EBV-negative cell line indicate that the compound specifically inhibits EBNA-1.

In the description below, we have described a preferred embodiment wherein the EBV-positive cell line is the 721 cell line and the EBV-negative cell line is the BJAB cell line (both available from the American Type Culture Collection). However, one of skill in the art, upon review of the present specification would understand that other B-lymphocyte cell lines may be substituted. Particularly useful cell lines would include carcinoma lines, such as gastric carcinoma cells and nasopharyngeal carcinoma cells. Applicants note that the cells, both EBV-negative and positive, must be proliferative.

One would begin to expose the cell lines to the test compound using a range of concentrations below that which is toxic in the EBV-negative test cells. This concentration range would be determined experimentally for each test compound.

Preferred test compounds that one may wish to examine include compounds that may be designed rationally to inhibit the DNA binding and dimerization domains of EBNA-1. These domains have been determined by X-ray crystallography and inhibitors of these domains activities may be designed.

The following is a description of a preferred embodiment of the assay:

The assay is based on the finding that the EBV-positive cell line 721 is induced to support apoptosis by infection with a retrovirus expressing a dominant negatively active derivate of EBNA-1 (termed "DNE1") but not by infection with a sister virus expressing β-galactosidase (termed "LacZ"). Each virus also encodes GFP such that infected cells can be sorted for expression of GFP and the 50% of the cells expressing the higher level of GFP sorted into 96 well plates. One would preferably optimize the efficiency of infection by screening EBV-positive cell lines in addition to 721 for those most efficiently infected as scored by the % GFP+ at 48 hours. The number of cells to be plated per well will be optimized for the assays to be used.

For example, if one used metabolic assays such as that termed "MTT," one might plate 1000–5000 cells per well and score for proliferation 6 days post-infection. At this time more than 30% of DNE1-infected cells may have undergone apoptosis so that a significant reduction of MTT-positive cells will be observed relative to LacZ-infected cells. (One would typically need approximately 10,000 viable cells to score positively in MTT assays.)

A typical assay to screen for inhibitors of EBNA that induce apoptosis is built on this observation because infection of EBV-negative cells with DNE1 has no effect. In one form of this assay, an optimum number of 721 cells will be distributed into 96 well plates as will the same number of EBV-negative cells, such as BJAB cells.

721 and BJAB cells will be treated in parallel with candidate test molecules, most preferably those designed, based on the known structure of EBNA-1, to inhibit its dimerization or DNA binding. By "treating" we mean to include the exposure of the cells to the test compound in solution or to the test compound as expressed or provided by an intracellular gene construct. Candidate test molecules may be selected from an available chemical library. Inhibit of proliferation, in this context, is likely to reflect an induction of apoptosis. By "induction of apoptosis" Applicants mean to include examination of proliferation as well as direct observation of apoptosis.

Compounds that inhibit proliferation of 721 cells but not BJAB cells will be pursued. In particular, the positive testing compounds may be assayed for their induction of apoptosis in multiple EBV-positive Burkitts lymphoma cell lines (AG876, Oku1) and their failure to induce apoptosis in multiple EBV-negative Burkitts lymphoma lines (BJAB, Kem1, DG75).

The MTT assay described above measures survival, and not apoptosis, but is convenient for large scale screens. To measure apoptosis directly, treated cells could be scored for active caspase 3, which is diagnostic of apoptosis. In one embodiment, EBV-positive and negative cells could be treated with candidate compounds and at 3–6 days post-treatment stained for expression of active caspase 3 with specific antibodies and examined by immunofluorescence. Compounds that inhibit EBNA's function by, for example, inhibiting is dimerization or DNA-binding should induce apoptosis only in the EBV-positive cells. Such compounds are clearly candidates for treating EBV-associated diseases.

Applicants note that they mean to observe "significant" apoptosis and by "significant" they mean to indicate that background levels of apoptosis, typically between 3%–5%, are usually present in a cell population. A preferred embodiment of the method of the present invention requires that the apoptosis level of the EBV-negative cell line be at least 2-fold, and preferably 10-fold, greater than that of the EBV-negative cell line.

In another embodiment, the present invention is a kit comprising an EBV-negative cell line, an EBV-positive cell line and instructions for the assay.

EXAMPLES

We have tested whether EBNA-1 is essential for the maintenance of cell proliferation of EBV-positive B-cells. Dominant-negative derivatives of EBNA-1 have been shown to inhibit EBNA-1's support of both replication and transcription of engineered vectors in short-term experiments (Kirchmaier and Sugden, 1997; Mackey and Sugden, 1999). Here we show that the introduction of one of the dominant-negative mutants specifically inhibits proliferation of EBV-immortalized normal B-cell lines and EBV-positive Burkitt's lymphoma cell lines. EBNA-1 is thus required for the maintenance of proliferation of EBV-infected B-cell lines. We have found that the mechanism of this inhibition unexpectedly includes the induction of apoptosis. We have asked whether viral genes in addition to EBNA-1 are required for the inhibition of apoptosis and found that EBNA-1 alone can inhibit apoptosis induced by p53 in EBV-negative cells. Inhibiting EBNA-1 should inhibit proliferation and induce apoptosis in EBV-positive B-cell tumors in patients. It is desirable to develop such inhibitors to test clinically.

Results

Inhibition of EBV-dependent cell proliferation by a dominant-negative derivative of EBNA-1. To test directly whether EBNA-1 is essential for maintaining cell proliferation, we introduced a dominant-negative derivative of EBNA-1, DNE1, which consists of EBNA-1's nuclear localization signal (NLS) and its overlapping dimerization and DNA binding domain (FIG. 1A), into B-cells with a pantropic murine leukemia virus-based vector (FIG. 1B) (Kirchmaier and Sugden, 1997; Ory, et al. 1996). A parallel vector expressing β-galactosidase (lacZ) in place of the DNE1 was used as a control throughout these studies. Both vectors also express green fluorescent protein (GFP) from an internal ribosomal entry site (IRES). Two days post-infection, GFP-positive cells were sorted by FACS into 96-well plates. Western blot analyses demonstrated that the DNE1 was expressed in infected cells (FIG. 2A), and assays for β-galactosidase showed that lacZ was expressed in parallel as well (data not shown and FIG. 3). We infected three EBV-positive normal B-cells and fourteen EBV-positive or -negative Burkitt's lymphoma cell lines with lacZ- or DNE1-expressing retroviruses (lacZ- or DNE1-virus), and measured their abilities to proliferate in limiting dilution assays. Between 0.1% and 70% of the cells infected with the control virus formed colonies depending upon the cell line tested. We compared these cloning efficiencies with those of the same cells infected with the DNE1-virus in parallel (Table 1). Six EBV-negative Burkitt's lymphoma cell lines showed no apparent difference in their cloning efficiencies when infected with these viruses (the average ratio of the cloning efficiencies±standard deviation was 1.03±0.29). However, in ten of eleven tested cell lines fewer EBV-positive cells survived to yield clones when infected with the DNE1-virus than when infected with the lacZ-virus. The one exception, Raji cells, has been in cell culture for more than 30 years and has presumably evolved far from the initial tumor (Pulvertaft and Pulvertaft, 1967). These findings indicate that the disruption of EBNA-1's function by DNE1 specifically inhibits proliferation of EBV-positive cells ($p<0.001$, Mann-Whitney's U test). The measured inhibition of proliferation by infection with the DNE1-virus does not appear to correlate with the abilities of the different control cells to proliferate under the conditions of the limiting dilution assays (Table 1A). We tested directly if increasing the cloning efficiencies in our assays of three cell lines would affect their survival after infection with the LacZ- and DNE1-viruses. Infected cells were plated on feeder layers of gamma-ray-irradiated human fibroblast cells, which increased their cloning efficiencies 4- to 75-fold. Under these conditions proliferation of EBV-negative Ramos cells was unaffected by infection with either virus while EBV-positive AG876-J1 and Oku1 cells were inhibited similarly in their proliferation after infection with the DNE1-virus (Table 1B).

It is particularly striking that a requirement for EBNA-1 for cell proliferation extends even to Namalwa, a Burkitt's lymphoma cell line that has only integrated copies of EBV DNA ($p<0.05$, Mann-Whitney's U test), and to both Daudi and P3HR-1/GG68 Burkitt's lymphoma cell lines, which have been propagated and subcloned in culture for decades ($p<0.05$, Mann-Whitney's U test) (Heston, et al., 1982; Klein, et al., 1968; Lawrence, et al., 1988)). Infection of Namalwa cells with the DNE1-virus results in an inhibition of proliferation that does not require loss of the viral genome and may result in part from an inhibition of EBNA-1's support of transcription.

Figure 2:
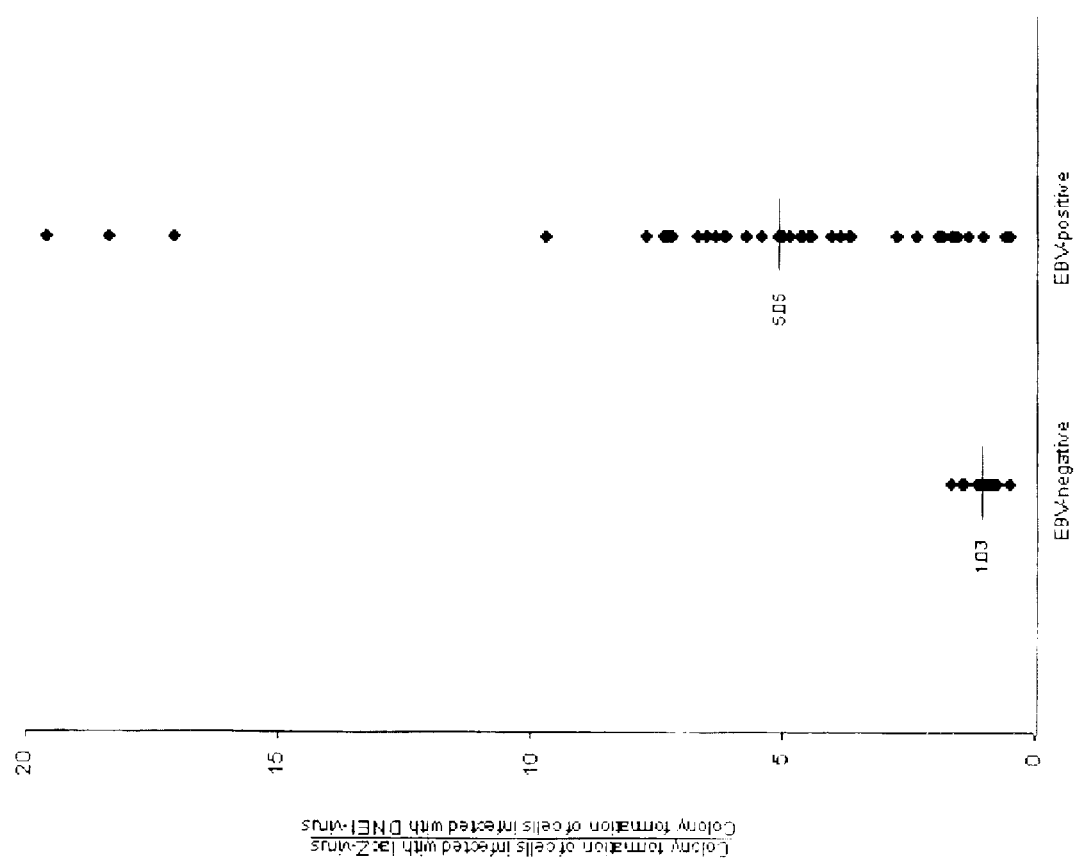
FIG. 2. Graphical presentation of the efficiency with which infection by DNE1-virus inhibits proliferation. The colony formation of cells infected with lacZ-virus divided by that for cells infected by DNE1-virus from all independent assays is shown. The average and standard deviation for the EBV-negative and -positive are $1.03\pm0.29$ and $5.05\pm5.04$, respectively ($P<0.001$, Mann-Whitney's U test).

The DNE1-virus inhibits proliferation of EBV-positive cells dose-dependently. Not all EBV-positive cells infected with the DNE1-virus cease to proliferate. Those cells that continue to proliferate can express the DNE1 protein (FIG. 3A). We tested whether these DNE1-positive cells proliferate possibly because of a low level of expression of the DNE1 protein. The level of β-galactosidase activity in LacZ-infected BJAB cells was demonstrated to correlate with the level of the downstream IRES-driven GFP expression (Table 2A). We then collected retrovirus-infected, EBV-positive RPMI1788 cells expressing varying levels of GFP. The levels of GFP expressed in DNE1-virus-infected 1788 cells were inversely proportional to their abilities to survive and proliferate in limiting dilution assays, whereas the levels of GFP-expression in lacZ-virus-infected cells were unrelated to their proliferation (Table 2B). These findings indicate that inhibition of cell proliferation by DNE1 is directly proportional to the amount of protein expressed. A prediction of this dose-dependent inhibition is that EBV-positive cells that survive infection with DNE1 would preferentially express low levels of the dominant negative mutant and of GFP. We tested this prediction by comparing the levels of GFP in cells sorted at 2 days post-infection with those of surviving clones at 5–6 weeks post-infection in both EBV-negative DG75 cells and in EBV-positive 721 cells infected with both retroviruses. The average intensity of GFP expression in the DNE1-virus- and lacZ-virus-infected DG75 cells shifted similarly around the threshold level of expression used to sort the cells from early to late times after infection, in 27 clones infected with LacZ and 24 clones infected with DNE1 ($p=0.15$). In 721 cells, the distribution of GFP-expression in DNE1-virus-infected cells did not evolve as in lacZ-virus-infected cells. The surviving DNE1-virus-infected 721 cells (16 clones tested) expressed lower levels of the DNE1 protein, as reflected by GFP expression, than those cells infected with lacZ-virus (13 clones tested) ($p<0.01$, Fisher's exact test). These findings demonstrate that EBV-positive cells that escape the inhibitory effects of the DNE1-provirus are those in which the DNE1 is expressed inefficiently. The anti-proliferative effect of inhibiting EBNA-1 is dose-dependent but compelling (FIG. 2).

The inhibition of EBNA-1 can select for loss of EBV DNA. It is particularly surprising that infection with the DNE1-virus inhibits proliferation even in the Burkitt's lymphoma cell line, Akata, which has been previously shown to yield surviving EBV-negative clones ($p<0.05$, Mann-Whitney's U test) (Shimizu, et al., 1994). We tested whether the surviving DNE1-virus-infected Akata cells retained EBV DNA. Five of eight of these DNE1-positive clones had lost their EBV DNA, whereas all five lacZ-virus-infected Akata clones retained their EBV DNA (FIG. 3B). On the other hand, EBV DNA was detected similarly in lacZ- and DNE1-virus-infected 721 cells (FIG. 3B). Most EBV-positive cells are akin to 721 and have not been shown to be able to lose their viral genome and still proliferate. We examined additional Akata clones infected with both lacZ- and DNE1-virus by immunofluorescence. In summary, 1 of 12 lacZ-virus-infected Akata clones was EBNA-1-negative, but 9 of 12 DNE1-virus-infected Akata clones were EBNA-1-negative. The frequency of isolating EBNA-1-negative clones was significantly higher in DNE1-virus-infected cells than that in lacZ-virus-infected cells ($p=0.003$, Fisher's exact test). Clearly, the expression of DNE1 facilitates the loss of EBV's genome in these uncommon EBV-positive cells that can survive without maintaining the viral genome. Still the inhibition of EBNA-1 in these uncommon EBV-positive cells inhibits their proliferation (Table 1A).

Figure 4:
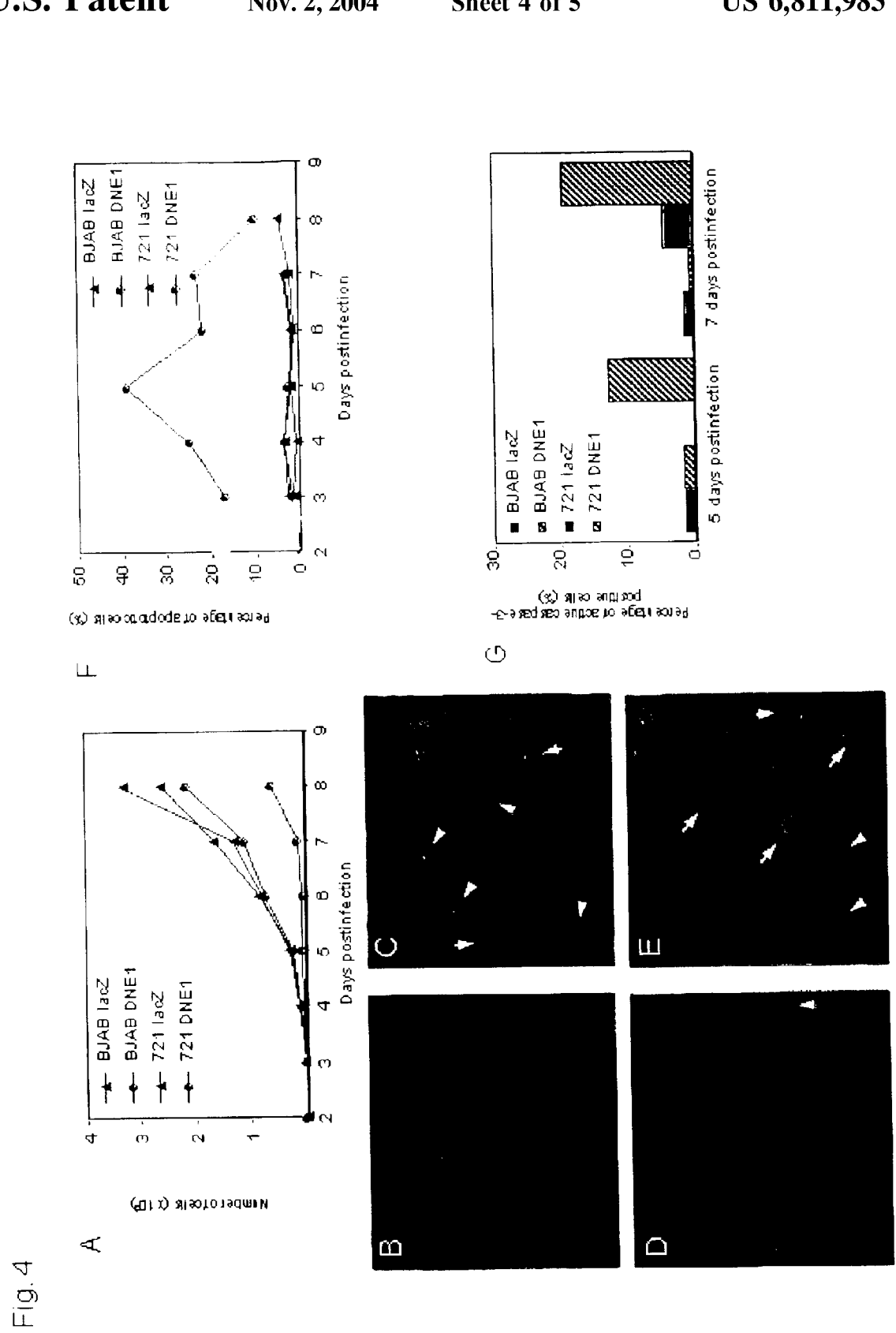
FIG. 4. Infection with DNE1-virus induces apoptosis in EBV-positive cells.

The inhibition of EBNA-1 can induce apoptosis in EBV-positive cells. We examined the fate of DNE1-virus-infected, EBV-positive cells to determine the mechanism by which they fail to proliferate. We assayed the proliferation of EBV-negative BJAB cells and EBV-positive 721 cells infected with either lacZ- or DNE1-viruses by counting the number of cells after sorting. LacZ- and DNE1-virus-infected BJAB cells proliferated similarly, while DNE1-infected 721 cells grew more slowly than did lacZ-virus-infected 721 cells (FIG. 4). Similar results were observed in four EBV-positive cell lines AG876-J1, Daudi, Oku I, and RPMI1788, whereas Kem I, an EBV-negative Burkitt's lymphoma cell line, behaved as did BJAB cells. EBV-positive cells would be killed were virus to undergo productive infection in them. We therefore assayed cells for the expression of viral lytic antigens and detected a background staining in 1.5% and 1.9% in lacZ- and DNE1-virus infected 721 cells at 3 days post-infection, respectively, indicating that the inhibition of EBNA-1 does not induce EBV's lytic cycle. Analysis of the nuclear morphology of these cells was revealing however; staining them with DNA-specific dye Hoechst 33342 and propidium iodide showed that up to 39% of DNE1-virus-infected 721 cells displayed the nuclear morphology characteristic of apoptosis at 3–7 days post-infection. The percentage of apoptotic cells in lacZ-virus-infected 721 cells was less than 4.6% (FIGS. 4B–F). The induction of apoptosis in EBV-positive cells by the inhibition of EBNA-1 was confirmed with immunofluorescent assays by using an antibody to active caspase-3 and by flow cytometric analysis, measuring sub G0/G1 DNA content (FIG. 4G and Table 3A). Infection with the DNE1-virus induced apoptosis in the EBV-positive cells AG876-J1, Akata, Daudi, Oku I, and RPMI1788, but not in Kem I cells, which are EBV-negative (Table 3A). These data demonstrate that one means by which interfering with EBNA-1's functions inhibits the growth of EBV-positive cells is to induce apoptosis in them. Induction of apoptosis by infection with the DNE1-virus in 721 cells was detected as early as 24 hours post-infection making it unlikely that the viral genome need be lost to induce apoptosis (Table 3B). Twenty-four hours encompasses one mitosis during which the retrovirus can integrate and express the dominant, negative mutant but not a second mitosis during which the viral plasmid might be expected to be lost. We have detected viral DNA in cells early in apoptosis. 721 cells infected with DNE1-virus were stained with both annexin V conjugated with Alexa Fluor 633, a marker for early apoptosis, and 4',6-diamindino-2-phenylindole (DAPI), a marker for the plasma membrane integrity. Approximately 17% of DNE1-virus-infected, annexin V-positive, DAPI-negative cells were isolated by FACS four days post-infection and found to contain EBV DNA by semi-quantitative PCR (data not shown). These findings indicate that inhibiting EBNA-1 can induce apoptosis in EBV-positive cells without the loss of viral DNA.

EBNA-1 prevents apoptotic cell death induced by p53 in SAOS-2 and VM-10 cell lines. Given that the inhibition of EBNA-1 can induce apoptosis, EBNA-1 itself can indirectly or directly prevent apoptosis. We have therefore tested the hypothesis that EBNA-1 can directly prevent apoptosis in the absence of other EBV genes. The p53-negative osteosarcoma cell line SAOS-2 was transfected with a vector expressing p53 with or without ones expressing EBNA-1. Forty-eight hours post-transfection, the cells were stained with Hoechst dye and propidium iodide (PI) and the percentages of apoptotic cells were scored by morphological examination. The expression of p53 in SAOS-2 cells induced apoptosis in the cells which was prevented either by co-expression of the LANA gene of KSHV or by EBNA-1 (FIG. 5A). LANA has previously been shown to inhibit apoptosis mediated by p53 in these cells (Friborg, et al., 1999). This assay of the inhibition of apoptosis was corroborated by counting cells stained with annexin V conjugated to Alexa Fluor 645 by FACS analysis: in this assay the expression of p53 in SAOS-2 cells induced apoptosis in 14% of the cells which was reduced to 6% by co-expression of EBNA-1 or LANA. These observations were extended to a cell line in which p53 is endogenously expressed, VM-10. These cells were derived from a mouse embryonic fibroblast cell originally null for p53 and engineered to express a temperature sensitive mutant of p53 and the c-myc gene (Martinez, et al., 1991). VM-10 cells undergo low levels of spontaneous apoptosis (<5%) at 39° while at the permissive temperature of 32° C. the functioning of p53 induces apoptosis in up to 40±10% of the cells after 24 hours. The percent of apoptotic cells was determined by staining with annexin V detected by FACS. Again the introduction of plasmids expressing LANA or EBNA-1 decreased the temperature-induction of apoptosis from 30% to 12% of the cells (FIG. 5B). These assays in EBV-negative SAOS-2 and VM-10 cells demonstrate that EBNA-1 can inhibit apoptosis in the absence of other viral genes. Thus inhibiting EBNA-1 blocks its anti-apoptotic activity and is one means to stop proliferation of Burkitt's lymphoma and normal EBV-positive cells.

Discussion

Figure 5:
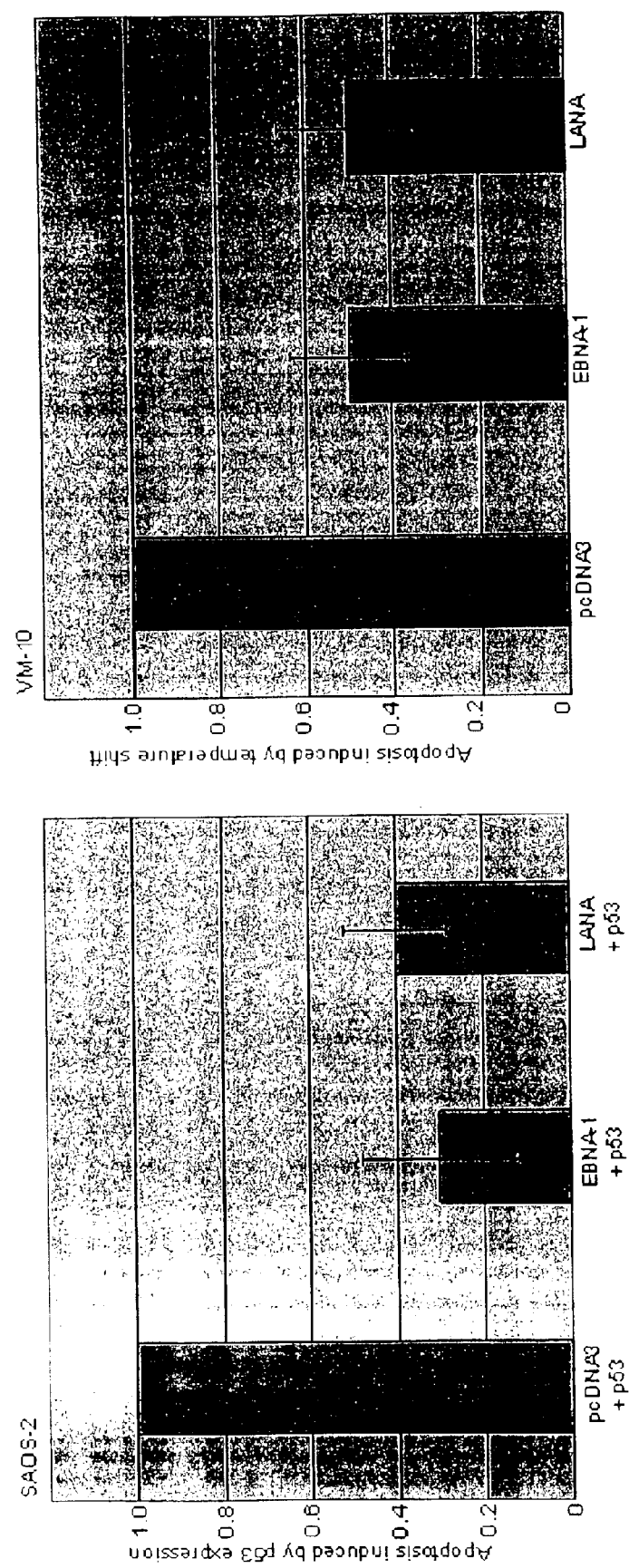
FIG. 5. EBNA-1 inhibits p53-mediated induction of apoptosis in SAOS-2 cells and VM-10 cells. The percent of cells undergoing apoptosis in the absence of EBNA-1 was determined in at least 3 independent experiments performed in duplicate and normalized to 1 (percent apoptosis in SAOS-2 and VM-10 in the absence of EBNA-1 was $16.8\pm3.9$ and $31.2\pm18.9$, respectively). The percent apoptosis in the presence of EBNA-1 expression was determined and is presented a ratio of apoptosis in the presence of EBNA-1 to the percent apoptosis in the absence of EBNA-1 (the percent apoptosis in SAOS-2 and VM-10 transfected with a plasmid DNA encoding EBNA-1 was 3.4±1.5 and 12.5±3.8, respectively). The Wilcoxson rank sum test was used to determine statistical significance of reduction in percent apoptosis by EBNA-1 and revealed p-values ≦0.01 in all cases.

The expression of a dominant-negative derivative of EBNA-1 via a retroviral vector, DNE1, inhibits proliferation of ten EBV-positive cell lines, but not six EBV-negative cell lines (Table1A, 1B, and FIG. 2). The inhibitory effects of the DNE1-virus are dose-dependent: higher levels of expression by the DNE1-virus inhibit EBV-positive cells more efficiently; DNE1-virus-infected EBV-positive cells that survive to proliferate express only low levels of DNE1. This specific inhibition demonstrates that EBNA-1 functions to maintain the proliferation of both EBV-immortalized normal B-cells and EBV-positive Burkitt's lymphoma cells. The disruption of EBNA-1's functions also results in the induction of apoptosis (Table3A, 3B, and FIG. 4). This finding indicates that EBNA-1 can inhibit apoptosis directly or indirectly. EBNA-1 does prevent apoptosis induced by the expression of p53 in SAOS-2 and VM-10 cells in the absence of other viral genes, which supports EBNA-1 directly inhibiting apoptosis (FIG. 5). Inhibiting EBNA-1 in those Burkitt's lymphoma cell lines which are p53-negative can induce apoptosis (Table 1) (Farrell, et al., 1991). We therefore think it likely that when EBNA-1 blocks apoptosis induced by p53 in SAOS-2 and VM-10 cells, it acts downstream of p53 itself.

We now can hypothesize why Burkitt's lymphoma cells retain EBV DNA while expressing only a limited number of viral genes. EBNA-1 provides these cells a survival advantage. We can also potentially explain the need for EBNA-1 to inhibit apoptosis in the viral life cycle. Freshly isolated primary B-cells spontaneously undergo apoptosis in culture (Vermes, et al., 1997). For EBV to induce and maintain proliferation in these cells it needs to inhibit this apoptosis and EBNA-1 may do so. This prediction can be tested by introducing vectors expressing EBNA-1 into primary B-cells to determine if the cells become more resistant to apoptosis then in EBNA-1's absence.

The inhibition of EBNA-1 in EBV-positive cells by the DNE1-virus is dose-dependent and, under our conditions, can lead to 30–95% of treated cells dying (Table 1 and FIG. 2). The use of a retroviral vector expressing DNE1 and GFP from a bicistronic message allowed the isolation by FACS of those cells which expressed the dominant, negative derivative of EBNA-1. This isolation facilitated our detection of EBNA-1's pivotal role in maintaining proliferation of EBV-infected normal and tumor cells. One recent study employed a cell-line engineered to express conditionally a dominant negative derivative of EBNA-1 and failed to detect an effect following expression of this mutant on cell proliferation (Kang, et al., 2001). This cell line carries its EBV DNA in an integrated state (Hurley, et al., 1991). Either idiosyncrasies of this cell line or its engineering, which may have inadvertently selected for cells resistant to the apoptosis induced by inhibiting EBNA-1, could have prevented detection of EBNA-1's contribution to proliferation.

Our findings have a striking parallel with those of Dan DiMaio and his colleagues who have found that inhibiting expression of the viral E6 and E7 genes in tumor cell lines infected with human papilloma viruses (HPV) inhibits their proliferation (Goodwin and DiMaio, 2001; Goodwin, et al., 2000). However, in the case of HPV-derived tumor cells, the inhibition of viral genes leads to death by senescence rather than by apoptosis. What is striking in these observations is that virus-induced tumor cells, which evolved over many generations in vivo and have been subsequently propagated for hundreds or thousands of generations in cell culture, still retain a requirement for viral survival factors.

Our findings lead to the tantalizing prospect that therapies directed against EBNA-1 should permit treatment of some or all EBV-associated cancers given that EBNA-1 is expressed in all known EBV-positive tumors. The specificity of DNE1's inhibitory effect on EBV-positive cells is advantageous because if used for gene therapy it would not require its sole targeting to tumor cells. A more efficient expression of the DNE1 could be achieved by introducing EBNA-1-binding sites and an appropriate promoter into a retroviral vector to foster high levels of expression of the DNE1 only in EBV-positive cells. A high level of expression of the DNE1 would be required for efficient killing of tumor cells. Alternatively, small molecule inhibitors of EBNA-1's dimerization or DNA-binding can be identified which should be efficient, potent inducers of apoptosis in EBV-positive tumors. Given that more than 90% of the human population is already infected with EBV and an increasing number of human cancers are being associated with EBV, the ability to target specifically a viral gene to treat EBV-associated tumors is particularly desirable.

Materials and Methods

Cell culture.

B-cells were maintained in RPMI1640 medium supplemented with 10% fetal bovine serum (Omega Scientific, Tarzana, Calif.), 200 units/ml penicillin, and 200 μg/ml streptomycin sulfate (GibcoBRL, Rockville, Md.). Okul, Kem I, Sav I were kindly provided by Dr. J. Sample (Nonkwelo, et al., 1997) (Ruf, et al., 1999). SAOS-2 is a p53-negative osteosarcoma cell line maintained in Dulbecco's modified Eagle's medium (high glucose) supplemented with 10% fetal bovine serum, 200 units/ml penicillin, and 200 μg/ml streptomycin sulfate, kindly provided by Dr. M. E. Perry. VM-10 is a cell line established through the stable transfection of the p53 null mouse embryo fibroblast cell line 10(1) with a DNA expressing a temperature-sensitive derivative of p53 and one expressing c-myc (Martinez, et al., 1991). VM-10 are maintained in Dulbeccos' modified Eagle's medium (high glucose) supplemented with 10% fetal bovine serum, 200 units/ml penicillin, and 200 μg/ml streptomycin sulfate, 0.5 μg/ml of G418, and 0.2 μ/ml of Hygromycin B. VM-10 was kindly provided by Dr. A. Levine. Cells were grown at 37° C. in the presence of a humidified, 5% $CO_2$ atmosphere.

Preparation of retrovirus vector and infection.

The dominant-negative EBNA-1 was described previously (plasmid 1160) (Kirchmaier and Sugden, 1997; Mackey and Sugden, 1999) Plasmids encoding lacZ- and DNE1-expressing retroviral vectors (plasmids 2840 and 2972) were transfected into 293 cells either by lipofectamine plus or lipofectamine 2000 (GibcoBRL) along with a VSV-G expression vector and a gag/pol expression vector (plasmids 2842 and 2843) (Ory, et al., 1996). Two to 6 days post-infection, culture supernatants were collected, filtered through a 0.45-μm filter, and stored at −80° C. Infection with the retroviruses was carried out as follows: cells were suspended in a retrovirus-containing medium at a concentration of $1\times10^6$/ml in the presence of 125–250 μg/ml of polybrene (Sigma, St. Louis, Mo.) and were incubated for 1 hour at 4° C. After incubation, cells were washed with fresh culture medium and incubated at 37° C.

Analyses of cells.

Infected cells were sorted by a FACS Vantage or DIVA (Beckton Dickinson, San Jose, Calif.) and the population of cells expressing the highest levels of GFP (top 10–50%) were collected. Different numbers (1–240) of cells were directly deposited into multiple wells of 96-well plates containing 250 μl of culture medium supplemented with 20 mM HEPES. Where feasible wells containing surviving and proliferating cells were identified visually. In some cases cell proliferation was scored as positive when more than $10^4$ cells emerged by day 17 post-plating, as measured by the color-metric cell proliferation assay (CellTiter 96 Aqueous One Solution Cell Proliferation Assay, Promega, Madison, Wis.). Fewer than $10^4$ proliferating cells per well were not detected in this assay under our conditions. The cloning efficiency or efficiency of colony formation is defined as the frequency of positive wells over total wells when only those wells in which single cells were plated are considered. When the cloning efficiency was less the 0.3 it was determined using the Poisson distribution to consider wells in which more than one cell were plated. When human fibroblast feeder layers were seeded on plates, deposited, proliferating cells were scored by visual inspection. To determine the rate of proliferation, 2500 GFP-positive cells were deposited in multiple wells of a 96-well plate and subsequently counted daily. To measure apoptosis following cell sorting, cells were collected from each well and stained with Hoechst 33342 (Sigma, St. Louis, Mo.) and propidium iodide (Sigma); the total number of cells and apoptotic cells were counted on a hemocytometer by fluorescent microscopy. For SAOS-2 and VM-10 cells, only GFP-positive cells were examined. For recording images, cells were fixed on a glass slide, stained with acridine orange, and images were captured by the Bio-Rad MRC 1024 confocal system (×600 magnification; Bio-Rad, Hercules, Calif.).

Annexin V Binding.

Cells were washed with phosphate-buffered saline (PBS), and suspended in 100 μl of a solution containing annexin V conjugated with Cy5 (Sigma) or Alexa flour 633/645 (Molecular Probes, Eugene, Oreg.) in a calcium-containing buffer according to the manufacturers' instructions. After incubation for 10 minutes at room temperature, PI or DAPI was added to a final concentration of 20 μg/ml. The samples were immediately analyzed on a hemocytometer with fluorescent microscopy or on a FACScalibur flow cytometer (Becton Dickinson). Data were collected in list mode, stored, and analyzed with Cell Quest software (Becton Dickinson).

Immunodetection of viral antigens.

For Western blot analysis, cells were washed three times with cold PBS and resuspended in PBS at a concentration of $2\times10^5/\mu l$. An equal volume of lysis buffer was added containing 4% sodium dodecyl sulfate (SDS), 100 mM Tris-HCl (pH 6.8), 12% 2-mercaptoethanol, 20% glycerol, and bromophenol blue. Samples were incubated at 95° C. for 10 minutes. Protein lysates approximately equivalent to $10^6$ cells were separated in SDS-polyacrylamide gel, transferred electrophoretically to a nitrocellulose membrane (Bio-Rad), and blocked with dried non-fat milk. For the primary antibody, a rabbit antiserum purified against the c-terminus of EBNA-1 was used to detect DNE1 and wild-type EBNA-1. For the secondary antibody, anti-rabbit antibody and alkaline phosphatase conjugated on dextran (K1396, Dako, Carpinteria, Calif.) was used. Signals were detected by incubating the blots in the presence of nitroblue tetrazolium (Fisher, Itasca, Ill.) and 5-bromo-4-chloro-3-indolyl-phosphate (Sigma). For immunofluorescent assays, cells were dried on a glass slide and fixed with 90% cold ethanol. Cells were incubated with human serum or anti-active caspase 3 antibody (Promega) for 1 hour at 37° C. in a humidified atmosphere, washed with PBS, incubated with anti-human complement 3 conjugated with fluorescein-isothiocyanate (Cappel, Aurora, Ohio) or biotinylated anti-rabbit goat antibody, followed by TexasRed-streptavidin (Vector Laboratories, Burlingame, Calif.). Cells were mounted in Vectashield anti-fade medium (Vector laboratories) and imaged by the Bio-Rad MRC 1024 confocal system (×600 magnification).

Southern blot analysis.

Cellular DNA was isolated by DNAzol (GibcoBRL). Ten microgram of DNA was digested with Bam HI, separated in 0.8% agarose gel, and transferred to a nylon membrane (HyBond N+, Amersham-Pharmacia, Piscataway, N.J.). DNA was fixed on the membrane with alkaline treatment (0.4 N NaOH for 20 minutes), and the Bam HI W fragment of EBV was detected with a cloned fragment as a probe. The signal was detected with the AlkPhosDirect system (Amersham-Pharmacia) according to the manufacturer's protocol.

Transfections into SAOS-2 and VM-10 cells.

For experiments in SAOS-2 cells, 1 ug of p53 expression plasmid (p3006) with 10 $\mu$g of either empty vector pcDNA3 (p1782) or EBNA-1 expression plasmid (p1553) and a plasmid encoding GFP (p2145) were transfected by the calcium phosphate precipitation method into the 10 cm tissue culture dish. Transfection of VM-10 was performed using either calcium phosphate precipitation or with the liposomal reagent Lipofectamine plus (Invitrogen, Carlsbad, Calif.) according to the manufacturer's instructions. Cells were plated in 6-well tissue culture plates at a concentration of $2.5\times10^5$ cells per well and transfected with a total of 6 $\mu$g of DNA.

TABLE 1

Expression of a dominant negative derivative of EBNA-1 inhibits proliferation only of EBV-positive cells.

| | | | A. | | | |
|---|---|---|---|---|---|---|
| Cells | Origin | EBV | Type of Latency | Average cloning efficiencies for lacZ-infected cells | Number of experiments | Cloning efficiencies (lacZ/DNE1)[b] |
| BJAB | BL | — | — | 66% | 4 | 0.9 ± ## |
| BJAB/EBNA-1 | BL | — | — | 39% | 2 | 0.9 ± ## |
| BL41 | BL | — | — | 1.3% | 2 | 1 4 ± ## |
| DG75 | BL | — | — | 79% | 2 | 1.2 ± ## |
| Kem 1 | BL | — | — | 60% | 3 | 0.9 ± 0 |
| Ramos | BL | — | — | 1.0% | 2 | 1.0 ± 1 |
| AG87G-J1 | BL | + | type I | 1.9% | 3 | 4.6 ± ## |
| Akata | BL | + | type I | 3.6% | 3 | 2.9 ± ## |
| Daudi | BL | + | type I | 14% | 3 | 4.6 ± ## |
| Oku I | BL | + | type I | 0.3% | 1 | ≧2.9 |
| Sav I | BL | + | type I | 0.2% | 1 | ≧2.3 |
| Namalwa | BL | + | type III | 3.1% | 4 | 3.0 ± ## |
| P3HR-1/GG68 | BL | + | type III | 2.3% | 3 | 1.4 ± ## |
| Raji | BL | + | type III | 7.3% | 2 | 0.7 ± ## |
| 721 | normal B cell | + | type III | 27% | 6 | 12.5 ± ## |
| RPMI1788 | normal B cell | + | type III | 9.2% | 2 | 4.1 ± ## |
| 11/17-3 | normal B cell | + | type III | 0.3% | 1 | ≧4.9 |

[a]The type of latency is defined by the profile of EBV latent genes expressed. In type I latency, EBNA-1, EBERs, and the transcript from the Bam HI A fragment of EBV DNA are expressed. In type III latency, all the EBNAs and LMPs are expressed in addition to those expressed in type I latency (reviewed in Crawford, 2001.
[b]Each number represents the average and the standard deviation of the cloning efficiencies of lacZ-virus-infected cells divided by that of DNE1-virus-infected cells from independent experiments.

TABLE 1-continued

Expression of a dominant negative derivative of EBNA-1 inhibits proliferation only of EBV-positive cells.

B.

| Cells | EBV | Percent cloning efficiencies of LacZ-infected feeder layer − | Percent cloning efficiencies of LacZ-infected feeder layer + | Fold increase (x) | Ratio of cloning efficiencies (lacZ/DNE1) (n) feeder layer − | Ratio of cloning efficiencies (lacZ/DNE1) (n) feeder layer + |
|---|---|---|---|---|---|---|
| Ramos | − | 1.0 (2) | 75 (2) | 75 | 1.0 (2) | 0.9 (2) |
| AG876-J1 | + | 1.9 (4) | 7.2 (2) | 4 | 4.6 (3) | 4.8 (2) |
| Oku I | + | 0.3 (1) | 20 (4) | 67 | ≧2.9 (2) | 7.1 (4) |

The average of cloning efficiencies for the lacZ-virus infected cells of the number of experiments (n) are shown. The cloning efficiencies and ratios of cloning efficiencies without feeder layer are adopted from Table 1.

TABLE 2

Inhibition of EBNA-1 decreases proliferation dose-dependently.

A. Correlation of the intensity of GFP and the beta/galactosidase activity in sorted BJAB cells.

| Mean GFP intensities | B-galactosidase activities immediately after sorting | B-galactosidase activities 13 days after sorting |
|---|---|---|
| 350 | 38450 | 22130 |
| 60 | 7070 | 10060 |
| 20 | 3400 | 4700 |
| 2 | 110 | 50 |

B. Increasing levels of DNE1 inhibits cell proliferation more efficiently in RPMI1788 cells.

| | Cloning Efficiency % | | |
|---|---|---|---|
| | 20% least green | 20% middle green | 20% most green |
| LacZ-infected 1788 | 3 | 4.4 | 4.4 |
| DNE1-infected 1788 | 1.8 | 1.1 | 0.45 |
| Ratio LacZ/DNE1 | 1.7 | 4 | 9.7 |

TABLE 3

Inhibition of EBNA-1 by DNE1 induces apoptosis in infected cells.

A. The percentage of apoptotic cells after infection with retroviral vectors.

| | | | Percent apoptotic cells | |
|---|---|---|---|---|
| Cells | EBV | Days post-infection | LacZ-virus-infected | DNE1-virus-infected |
| BJAB | — | 5–7 | 2.2 ± 1 (5); 1.5$^c$, 4.5$^f$ | 2.2 ± 1 (5) |
| Kem 1 | — | 7 | 1.4 | 1.6 |
| AG876-J1 | + | 6 | 4.0 | 15.2 |
| Akata | + | 7 | 3.2 ± 2.2 (2) | 6.4 ± 6.4 (2) |
| Daudi | + | 5 | 1.2 ± 0.3 (2) | 3.6 ± 0.3 (2) |
| Oku I | + | 5 | 6.9 | 18.4 |
| 721 | + | 4–7 | 1.8 ± 0.8 (6); 4.5$^c$, 2.3$^f$ | 79 ± 9.2 (5); 19.5$^c$, 19.5$^f$ |
| RPMI1788 | + | 5 | 4.4 | 10.2 |

The percentage of apoptotic cells in culture was determined by morphological examination *number of trials in parentheses) or an immunofluorescent assay against active caspase-3 (superscript c) or flow cytometric analysis (superscript f). DNE1-virus-infected EBV-positive cells had a significantly higher percentage of apoptotic cells than did lacZ-virus-infected cells (p < 0.001); no significant difference was seen between the EBV-negative cells infected with both viruses (p = 0.68. Wilcoxon's matched pairs signed-ranks test).

TABLE 3-continued

Inhibition of EBNA-1 by DNE1 induces apoptosis in infected cells.

B. Apoptosis can occur within 24 hours of infection with DNE1-virus.

| | | | Percent of apoptotic cells | | | |
|---|---|---|---|---|---|---|
| | | | expt 1 | | expt 2 | |
| Cells | EBV | Infecting retrovirus | morphology[a] | annexin V[b] | morphology | annexin V |

The percentage of apoptotic cells was scored by the morphological observation of cells Hoechst33342 and propidium iodide (superscript a) or by counting annexin V-positive cells after staining with Annexin V-Cy5 (superscript b). not; not tested.

REFERENCES

Bonnet, M., Guinebretiere, J. M., Kremmer, E., Grunewald, V., Benhamou, E., Contesso, G., and Joab, I. (1999). Detection of Epstein-Barr virus in invasive breast cancers, *J. Natl. Cancer Inst.* 91, 1376–81.

Chaudhuri, B., Xu, H., Todorov, I., Duffa, A., and Yates, J. L. (2001). Human DNA replication initiation factors, ORC and MCM, associate with oriP of Epstein-Barr virus, *Proc. Natl. Acad. Sci. USA* 98, 10085–9.

Cohen, J. I., Wang, F., Mannick, J., and Kieff, E. (1989). Epstein-Barr virus nuclear protein 2 is a key determinant of lymphocyte transformation, *Proc. Natl. Acad. Sci. USA* 86, 9558–62.

Crawford, D. H. (2001), Biology and disease associations of Epstein-Barr virus, *Philos. Trans. R Soc. Lond. B Biol. Sci.* 356, 461–73.

de-The, G., Geser, A., Day, N. E., Tukei, P. M., Williams, E. H., Beri, D. P., Smith, P. G., Dean, A. G., Bronkamm, G. W., Feorino, P., and Henle, W. (1978). Epidemiological evidence for causal relationship between Epstein-Barr virus and Burkitt's lymphoma from Ugandan prospective study, *Nature* 274, 756–61.

Farrell, P. J., Allan, G. J., Shanahan, F., Vousden, K. H., and Crook, T. (1991). p53 is frequently mutated in Burkitt's lymphoma cell lines, *EMBO* 10, 2879–87.

Fina, F., Romain, S., Ouafik, L., Palmari, J., Ben Ayed, F., Benharkat, S., Bonnier, P., Spyratos, F., Foekens, J. A., Rose, C., Buisson, M., Gerard, H., Reymond, M. O., Seigneurin, J. M., and Martin, P. M. (2001). Frequency and genome load of Epstein-Barr virus in 509 breast cancers from different geographical areas, *Br. J. Cancer* 84, 783–90.

Friborg, J., Jr., Kong, W., Hottiger, M. O., and Nabel, G. J. (1999). p53 inhibition by the LANA protein of KSHV protects against cell death, *Nature* 402, 889–94.

Gahn, T. A., and Sugden, B. (1995). An EBNA-1-dependent enhancer acts from a distance of 10 kilobase pairs to increase expression of the Epstein-Barr virus LMP gene, *J. Virol.* 69, 2633–6.

Glaser, S. L., Lin, R. J., Stewart, S. L., Ambinder, R. F., Jarrett, R. F., Brousset, P., Pallesen, G., Gulley, M. L., Khan, G., O'Grady, J., Hummel, M., Preciado, M. V., Knecht, H., Chan, J. K., and Claviez, A. (1997). Epstein-Barr virus-associated Hodgkin's disease: epidemiologic characteristics in international data, *Int. J. Cancer* 70, 375–82.

Goodwin, E. C., and DiMaio, D. (2001). Induced senescence in HeLa cervical carcinoma cells containing elevated telomerase activity and extended telomeres, *Cell Growth Differ.* 12, 525–34.

Goodwin, E. C., Yang, E., Lee, C. J., Lee, H. W., DiMaio, D., and Hwang, E. S. (2000). Rapid induction of senescence in human cervical carcinoma cells, *Proc. Natl. Acad. Sci. USA* 97, 10978–83.

Hammerschmidt, W., and Sugden, B. (1989). Genetic analysis of immortalizing functions of Epstein-Barr virus in human B lymphocytes, *Nature* 340, 393–7.

Hanto, D. W., Frizzera, G., Purtilo, D. T., Sakamoto, K., Sullivan, J. L., Saemundsen, A. K., Klein, G., Simmons, R. L., and Najarian, J. S. (1981). Clinical spectrum of lymphoproliferative disorders in renal transplant recipients and evidence for the role of Epstein-Barr virus, *Cancer Res.* 41, 4253–61.

Heston, L., Rabson, M., Brown, N., and Miller, G. (1982). New Epstein-Barr virus variants from cellular subclones of P3J-HR-1 Burkitt lymphoma, *Nature* 295. 160–3.

Hurley, E. A., Klaman, L. D., Agger, S., Lawrence, J. B., and Thorley-Lawson, D. A. (1991). The prototypical Epstein-Barr virus-transformed lymphoblastoid cell line IB4 is an unusual variant containing integrated but no episomal viral DNA, *J. Virol.* 65, 3958–63.

Imai, S., Koizumi, S., Sugiura, M., Tokunaga, M., Uemura, Y., Yamamoto, N., Tanaka, S., Sato, E., and Osato, T. (1994). Gastric carcinoma: monoclonal epithelial malignant cells expressing Epstein-Barr virus latent infection protein, *Proc. Natl. Acad. Sci. USA* 91, 9131–5.

Kang, M. S., Hung, S. C., and Kieff, E. (2001). Epstein-Barr virus nuclear antigen 1 activates transcription from episomal but not integrated DNA and does not alter lymphocyte growth, *Proc. Natl. Acad. Sci. USA* 98, 15233–8.

Kaye, K. M., Izumi, K. M., and Kieff, E. (1993). Epstein-Barr virus latent membrane protein 1 is essential for B-lymphocyte growth transformation, *Proc. Natl. Acad. Sci. USA* 90, 9150–4.

Kempkes, B., Spitkovsky, D., Jansen-Durr, P., Ellwart, J. W., Kremmer, E., Delecluse, H. J., Rottenberger, C., Bornkamm, G. W., and Hammerschmidt, W. (1995). B-cell proliferation and induction of early G1-regulating proteins by Epstein-Barr virus mutants conditional for EBNA2, *EMBO J.* 14, 88–96.

Kilger, E., Kieser, A., Baumann, M., and Hammerschmidt, W. (1998). Epstein-Barr virus-mediated B-cell proliferation is dependent upon latent membrane protein 1, which simulates an activated CD40 receptor, *EMBO J.* 17, 1700–9.

Kirchmaier, A. L., and Sugden, B. (1997). Dominant-negative inhibitors of EBNA-1 of Epstein-Barr virus, *J. Virol.* 71, 1766–75.

Klein, E., Klein, G., Nadkarni, J. S., Nadkarni, J. J., Wigzell, H., and Clifford, P. (1968). Surface IgM-kappa specificity on a Burkitt lymphoma cell in vivo and in derived culture lines, *Cancer Res.* 28, 1300–10.

Lawrence, J. B., Villnave, C. A., and Singer, R. H. (1988). Sensitive, high-resolution chromatin and chromosome mapping in situ: presence and orientation of two closely integrated copies of EBV in a lymphoma line, *Cell* 52, 51–61.

Mackey, D., and Sugden, B. (1999). The linking regions of EBNA1 are essential for its support of replication and transcription, *Mol. Cell Biol.* 19, 3349–59.

Martinez, J., Georgoff, I., and Levine, A. J. (1991). Cellular localization and cell cycle regulation by a temperature-sensitive p53 protein, *Genes Dev.* 5, 151–9.

Nonkwelo, C., Ruf, I. K., and Sample, J. (1997). Interferon-independent and -induced regulation of Epstein-Barr virus EBNA-1 gene transcription in Burkitt lymphoma, *J. Virol.* 71, 6887–97.

Ory, D. S., Neugeboren, B. A., and Mulligan, R. C. (1996). A stable human-derived packaging cell line for production of high titer retrovirus/vesicular stomatitis virus G pseudotypes, *Proc. Natl. Acad. Sci. USA* 93, 11400–6.

Pulvertaft, R. J., and Pulvertaft, I. (1967). Activation of lymphocytes, *J. Clin. Pathol.* 20, 795–805.

Rawlins, D. R., Milman, G., Hayward, S. D., and Hayward, G. S. (1985). Sequence-specific DNA binding of the Epstein-Barr virus nuclear antigen (EBNA-1) to clustered sites in the plasmid maintenance region, *Cell* 42, 859–68.

Rowe, D. T. (1999). Epstein-Barr virus immortalization and latency, *Front Biosci.* 4, D346–71.

Ruf, I. K., Rhyne, P. W., Yang, H., Borza, C. M., Hutt-Fletcher, L. M., Cleveland, J. L., and Sample, J. T. (1999). Epstein-Barr Virus regulates c-MYC, apoptosis, and tumorigenicity in Burkitt lymphoma, *Mol. Cell Biol.* 19, 1651–60.

Schepers, A., Ritzi, M., Bousset, K., Kremmer, E., Yates, J. L., Harwood, J., Diffley, J. F., and Hammerschmidt, W. (2001). Human origin recognition complex binds to the region of the latent origin of DNA replication of Epstein-Barr virus, *EMBO J.* 20, 4588–602.

Shibata, D., and Weiss, L. M. (1992). Epstein-Barr virus-associated gastric adenocarcinoma, *Am. J. Pathol.* 140, 769–74.

Shimizu, N., Tanabe-Tochikura, A., Kuroiwa, Y., and Takada, K. (1994). Isolation of Epstein-Barr virus (EBV)-negative cell clones from the EBV-positive Burkitt's lymphoma (BL) line Akata: malignant phenotypes of BL cells are dependent on EBV, *J. Virol.* 68, 6069–73.

Siebert, J. D., Ambinder, R. F., Napoli, V. M., Quintanilla-Martinez, L., Banks, P. M., and Gulley, M. L. (1995). Human immunodeficiency virus-associated Hodgkin's disease contains latent, not replicative, Epstein-Barr virus, *Hum. Pathol.* 26, 1191–5.

Sugden, B., and Warren, N. (1989). A promoter of Epstein-Barr virus that can function during latent infection can be transactivated by EBNA-1, a viral protein required for viral DNA replication during latent infection, *J. Virol.* 63, 2644–9.

Tokunaga, M., Land, C. E., Uemura, Y., Tokudome, T., Tanaka, S., and Sato, E. (1993). Epstein-Barr virus in gastric carcinoma, *Am. J. Pathol.* 143, 1250–4.

Tomkinson, B., Robertson, E., and Kieff, E. (1993). Epstein-Barr virus nuclear proteins EBNA-3A and EBNA-3C are essential for B-lymphocyte growth transformation, *J. Virol.* 67, 2014–25.

Vermes, I., Haanen, C., Richel, D. J., Schaafsma, M. R., Kalsbeek-Batenburg, E., and Reutelingsperger, C. P. (1997). Apoptosis and secondary necrosis of lymphocytes in culture, *Acta Haematol.* 98, 8–13.

Yates, J. L., Warren, N., and Sugden, B (1985). Stable replication of plasmids derived from Epstein-Barr virus in various mammalian cells, *Nature* 313, 812–15.

Zeng, Y. (1985). Seroepidemiological studies on nasopharyngeal carcinoma in China, *Adv. Cancer Res.* 44, 121–38.

Zeng, Y., Zhong, J. M., Li, L. Y., Wang, P. Z., Tang, H., Ma, Y. R., Zhu, J. S., Pan, W. J., Liu, Y. X., Wei, Z. N., and et al. (1983). Follow-up studies on Epstein-Barr virus IgA/VCA antibody-positive persons in Zangwu County, China, *Intervirology* 20, 190–4.

Zimber-Strobi, U., Kempkes, B., Marschall, G., Zeidler, R., Van Kooten, C., Banchereau, J., Bornkamm, G. W., and Hammerschmidt, W. (1996). Epstein-Barr virus latent membrane protein (LMP1) is not sufficient to maintain proliferation of B cells but both it and activated CD40 can prolong their survival, *EMBO J.* 15, 7070–8.

We claim:

1. A method of assaying potential inhibitors of EBNA-1 comprising the steps of:
   (a) obtaining an EBV-positive cell line and an EBV-negative cell line wherein both cell lines are proliferative B-lymphocyte cell lines;
   (b) treating the cell lines with a test compound by exposure of the cells to the test compound in solution or to the test compound as expressed or provided by an intracellular gene construct, and
   (c) examining either cell proliferation or induction of apoptosis in the cell lines, wherein significant apoptosis or decrease in cell proliferation in the EBV-positive cell line and lack of significant apoptosis or increase in cell proliferation in the EBV-negative cell line indicates that the compound specifically inhibits EBNA-1.

2. The method of claim 1 wherein the EBV-positive cell line comprises 721 cells.

3. The method of claim 1 wherein the EBV-negative cell line comprises BJAB cells.

4. The method of claim 1 wherein the examining of step (c) comprises the step of examining cell proliferation.

5. The method of claim 1 wherein the examining of step (c) comprises the step of examining apoptosis.

6. The method of claim 1 wherein step (b) comprises exposure of the cell line to a test compound, wherein the test compound is added to a culture medium in which the cell lines are proliferating.

7. The method of claim 1 wherein the test compound is selected from a chemical library.

8. The method of claim 1 wherein the EBV-positive cell line is selected from the group consisting of AG876 cells and Oku I cells.

9. The method of claim 1 wherein the EBV-negative cell is selected from the group consisting of BJAB cells and DG75 cells.

* * * * *